US007410955B2

(12) United States Patent
Kim et al.

(10) Patent No.: US 7,410,955 B2
(45) Date of Patent: Aug. 12, 2008

(54) THERAPEUTIC USE OF AGONIST LIGANDS SPECIFIC TO G2A RECEPTOR

(75) Inventors: Yung-Hi Kim, Kangwon-do (KR); Dong-Keun Song, Kangwon-do (KR); Hong-Won Suh, Kangwon-do (KR); Sung-Oh Huh, Kangwon-do (KR)

(73) Assignee: Biosynergen, Inc., Chunchon, Kangwon-Do (KR)

( * ) Notice: Subject to any disclaimer, the term of this patent is extended or adjusted under 35 U.S.C. 154(b) by 0 days.

(21) Appl. No.: 10/509,300

(22) PCT Filed: Mar. 25, 2003

(86) PCT No.: PCT/KR03/00593

§ 371 (c)(1),
(2), (4) Date: Sep. 24, 2004

(87) PCT Pub. No.: WO03/080071

PCT Pub. Date: Oct. 2, 2003

(65) Prior Publication Data

US 2005/0288254 A1    Dec. 29, 2005

(30) Foreign Application Priority Data

Mar. 25, 2002 (KR) .................... 10-2002-0016029
Aug. 22, 2002 (KR) .................... 10-2002-0049766
Oct. 21, 2002 (KR) .................... 10-2002-0064308

(51) Int. Cl.
*A61K 31/665* (2006.01)
(52) U.S. Cl. ................................... 514/77
(58) Field of Classification Search .............. None
See application file for complete search history.

(56) References Cited

U.S. PATENT DOCUMENTS 4,746,652 A * 5/1988 Buckalew et al. ............ 514/77

(Continued)

FOREIGN PATENT DOCUMENTS

WO    WO 02/24222 A2    3/2002

(Continued)

OTHER PUBLICATIONS

Riedermann et al. Anti-inflammatory strategies for the treatment of sepsis. Expert Opin. Biol. Ther. (2003) 3(2):339-350.*

(Continued)

*Primary Examiner*—Ardin Marschel
*Assistant Examiner*—James D Anderson
(74) *Attorney, Agent, or Firm*—Michael Best & Friedrich LLP

(57) ABSTRACT

The present invention relates to novel therapeutical use of agonist ligands specific to G2A receptor. More particularly, the present invention relates to methods for treating a disease or disorder associated with neutrophil accumulation and hyperactivity and/or excessive release of IL-8, or with microbial infection, in a subject, comprising administering LPC (lysophosphatidylcholine), SPC(sphingophosphorylcholine) or derivatives thereof to the subject. The agonist ligands for G2A receptor according to the present invention and pharmaceutical- or therapeutical composition comprising said ligands can be used effectively in treatment of a disease or disorder associated with neutrophil accumulation and hyperactivity and/or excessive release of IL-8, specifically inflammatory diseases and diseases associated with ischemia-reperfusion injury as well as microbial infection.

2 Claims, 11 Drawing Sheets

U.S. PATENT DOCUMENTS 6,207,412 B1    3/2001    Weng et al.

FOREIGN PATENT DOCUMENTS

WO    WO 02/092104    11/2002

OTHER PUBLICATIONS

Rikitake et al. Expression of G2A, a Receptor for Lysophosphatidylcholine by Macrophages in Murine, Rabbit and Human Atherosclerotic Plaques. Arterioscler Thromb Vasc Biolo (2002) p. 2049-2053.*

Falcone et al. Ascaris suum-Derived Products Induce Human Neutrophil Activation via a G Protein-Coupled Receptor that Interacts with the Interleukin-8 Receptor Pathway. Infection and Immunity (2001) vol. 69, No. 6 pp. 4007-4018.*

Oxford English Dictionary Online© Oxford University Press (2007).*

Yan et al. Therapeutic effects of lysophosphatidylcholine on experimental sepsis. Nature Medicine, 2004, vol. 10, No. 2, pp. 161-167.*

Carson M, and Lo D, "The Push-Me Pull-You of T Cell Activation" (2001) *Science* 293:618-619.

Kabarowski Jhs, et al., "Lysophosphatidylcholine as a Ligand for the Immunoregulatory Receptor G2A" (2001) *Science* 293(5530):702-705.

Zhu K, et al., "Sphingosylphosphorylcholine and Lysophosphatidylcholine Are Ligands for the G Protein-coupled Receptor GPR4" (2001) *J. Biol. Chem.* 276(44):41325-41335.

Heermeier K, et al., "Oxidized LDL Suppresses NF-$\kappa_1$B and Overcomes Protection from Apoptosis in Activated Epithelial Cells" (2001) *J. Am. Soc. Nephrol* 12:456-463.

Lu, Ql, et al., "Mice Lacking the Orphan G Protein-coupled Receptor G2A Develop a Late-Onset Autoimmune Syndrome" (2001) *Immunity* 14:561-571.

Fukushima N, et al. "Lysophospholipid Receptors" (2001) *Annu. Rev. Pharmacol. Toxicol.* 41:507-534.

Lynch Kr, et al., "Life on the Edg" (2001) *Trends in Pharmacol. Sci.* 20(12):473-475.

Xu Y, et al., "Sphingosylphosphorylcholine is a ligand for ovarian cancer G-protein-coupled receptor 1" (2000) *Nat. Cell. Biol.* 2(5):264-267.

Rikitake Y, et al., "Expression of G2A, a Receptor for Lysophosphatidylcholine, by Macrophages in Murine, Rabbit, and Human Atherosclerotic Plaques" (2002) *Arterioscler Thromb Vasc Biol.* 22:2049-2053.

* cited by examiner

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: forward primer for G2A receptor

<400> SEQUENCE: 1
gctcagcagg actcctcaat cag                                           23

<210> SEQ ID NO 2
<211> LENGTH: 20
<212> TYPE: DNA
<213> ORGANISM: Artificial Sequence
<220> FEATURE:
<223> OTHER INFORMATION: reverse primer for G2A receptor

<400> SEQUENCE: 2 cggtggttgtcatcttccta                                                20
```

```
<210> SEQ ID NO 3
<211> LENGTH: 18
<212> TYPE: DNA
<213> ORGANISM: Artificial Sequence
<220> FEATURE:
<223> OTHER INFORMATION: forward primer for GPR4 receptor

<400> SEQUENCE: 3 ggcaaccacacgtgggag                                                  18

<210> SEQ ID NO 4
<211> LENGTH: 19
<212> TYPE: DNA
<213> ORGANISM: Artificial Sequence
<220> FEATURE:
<223> OTHER INFORMATION: reverse primer for GPR4 receptor

<400> SEQUENCE: 4 tccagttgtcgtggtgcag                                                 19
```

THERAPEUTIC USE OF AGONIST LIGANDS SPECIFIC TO G2A RECEPTOR

FIELD OF THE INVENTION

The present invention relates to novel therapeutic use of agonist ligands specific to G2A receptor and more particularly, to methods for treating a disease or disorder associated with neutrophil accumulation and -hyperactivity and/or excessive release of IL-8, or an infectious disease in a subject, comprising administering LPC (lysophosphatidylcholine), SPC (sphingophosphorylcholine) or derivatives thereof into the subject.

BACKGROUND OF THE INVENTION

Inflammation is an important defense response occurring in body against pathogens, foreign substances and tissue injury. Inflammation accompanies systemic symptoms such as fever, weakness, loss of appetite and chill, or local symptoms such as redness, swelling, pain and dysfunction. Inflammation is divided into acute inflammation, subacute inflammation and chronic inflammation according to its duration. Acute inflammation reaction occurs in blood vessel and is mostly mediated by neutrophils. Especially, in the case of suppurative inflammation, remarkable increase of neutrophils is observed. Chronic inflammation is continued for several weeks or several months. It is different from acute inflammation in that injury and recovery of tissues occur at the same time (Robbins Pathological Basis of Disease by R. S. Cotran, V Kumar, and S. L. Robbins, W.B. Saunders Co., p. 75, 1989). Although chronic inflammation may be derived directly from acute inflammation, it generally results from continuous infections that cause prolonged hypersensitive reactions (ex., tuberculosis, syphilis, fungal infection), exposure to continuous endotoxin (ex., increased plasma lipids) or exotoxins (ex., silica, asbestos, tar, surgery sutures), or autoimmune response against self-tissues (ex., rheumatic arthritis, systemic lupus erythematosus, multiple sclerosis, psoriasis) and it can thus initiate insidious onset that proceeds as times goes by. Accordingly, chronic inflammation includes numerous medical symptoms such as rheumatic arthritis, restenosis, psoriasis, multicentric sclerosis, surgery synechia, tuberculosis and chronic inflammatory lung diseases (ex., asthma, pneumoconiosis, chronic occlusive lung disease, pulmonary fibrosis). Subacute inflammation refers to an inflammation between acute and chronic inflammations.

As main inflammatory diseases, there are rhinitis and sinusitis such as infectious rhinitis, allergic rhinitis, chronic rhinitis, acute sinusitis and chronic sinusitis; otitis media such as acute purulent otitis media and chronic purulent otitis media; pneumonia such as bacterial pneumonia, bronchopneumonia, lobar pneumonia, *Legionella* pneumonia and viral pneumonia; acute or chronic gastritis; enteritis such as infectious enterocolitis, Crohn's disease, idiopathic ulcerative colitis and pseudomembranous colitis; and arthritis such as pyogenic arthritis, tuberculous arthritis, degenerative arthritis and rheumatoid arthritis. In addition, there is sepsis that accompanies extreme systemic inflammatory reaction at early stage. This sepsis results from excessive reaction of hosts against endotoxin of gram-negative bacteria, etc. In prior arts, so as to treat sepsis, there have been used antibiotics and steroid preparations, but their effects are weak and thus the death rate of hosts due to septicemia is still high.

Also, excessive inflammation causes permanent injury of surrounding tissues, and acute respiratory distress syndrome (ARDS) is regarded as one of typical inflammatory diseases resulting from tissue injury by excessive inflammation. The ARDS is an acute hypoxemic respiratory failure due to pulmonary edema resulting from the increased permeability of alveolar capillary barrier. It is regarded as the most severe case in acute lung injury (ALI). Clinical symptoms that lead patients to the risk of ARDS are various, for example, trauma, bleedings or septicemia, and ARDS results from excessive systemic inflammation reaction due to these symptoms. Even though there have been conducted treatments such as treatment of hypoxia, endotracheal intubation, mechanical ventilation, etc., the death rate due to ARDS still reaches 50~70%. Circulating inflammatory cells, especially neutrophils, have been known to have an important role in initiation and development of acute lung injury, e.g., pulmonary edema, inflammation reaction, etc. (Abraham et al., *Am. J. Physiol.*, 279, L1137-L1145, 2000). Several scientists proved that neutrophils are extensively accumulated in lungs of ARDS patients (Weinacker & Vaszar, *Annu. Rev Med.*, 52: 221-37, 2001). These neutrophils, once activated, discharge proteases including matrix metalloproteinases and other mediators causing lung injury. Hence, if neutrophil accumulation in lung is suppressed, ARDS due to acute lung injury may be treated.

Multiple organ dysfunction syndrome (MODS) is a disease resulting from the complication of sepsis, etc. As examples of MODS, there can be included acute hepatic failure, acute renal failure, lung failure, gastrointestinal bleeding, etc. For the treatment of MODS, antibiotics and steroid preparations have been used, however, their effects are weak.

Meanwhile, neutrophils (also called 'polymorphonuclear leucocytes (PMNs)') are phagocytic cells that have an important role in host defense mechanism and occupy approximately 60% of leucocytes that are circulating in body. The membrane of neutrophils has receptors for hemopoietic growth factors such as GM-CSF (granulocyte macrophage-colony stimulating factor), G-CSF (granulocyte-colony stimulating factor), etc., G proteins involving in signal transduction associated with receptors for opsonin and chemotactic factors, ion channels associated with the ion exchange of $Na^+$, $K^+$, $Ca^{2+}$, etc., enzymes and phospholipids. Also, at the surface of neutrophils, there exist Fc receptors against an IgG antibody such as CD16 and CD32 and receptors to C3 complement proteins such as CR1 and CR3. Accordingly, antigens bound thereto can be easily recognized and eliminated. As within the granule of neutrophils, there are defensin associated with disinfection such as peroxidase, lactoferrin, leukocyte adhesion receptor and alkaline phosphatase, and bactericidal/permeability-increasing protein (BPI), which destroy infectious agents or are involved in the proceedings of inflammatory reaction. Besides, the neutrophils express cell adhesion proteins such as CD11a/CD18(LFA-1), selectin, etc., which have an important role in the movement of neutrophils in inflammatory reaction.

For a normal adult, neutrophils are produced in an amount of $0.85-1.6 \times 10^9$ cells/kg/day. After being produced and differentiated in bone marrow over approximately 14 days, they enter peripheral bloods and circulate there for about 6 hours. They penetrate then into tissues and die or are lost at mucous membranes after surviving for several days in the tissues. Neutrophils have a short half-life of about 6-10 hours and they are removed in macrophages by apoptosis. The neutrophil apoptosis occurs spontaneously or by the external stimulus. As a typical example of the external stimulus, there can be mentioned a Fas pathway. Fas is a substance similar to TNF receptor that exists at the surface of neutrophils, and it induces apoptosis via an FADD pathway in cells once it is stimulated by a Fas ligand. Caspase has been known to have an important role in such a pathway. Neutrophil apoptosis has been known to be delayed or suppressed by various inflammation mediators. Some reports proposed that the delay (suppression) of neutrophil apoptosis observed in ARDS is due to GM-CSF. However, the intracellular transduction pathway that delays apoptosis of neutrophil had been hardly known. That is, in several inflammatory diseases, various inflammation mediators suppress neutrophil apoptosis that is physiologically and actively occurring, and consequently, continuous inflammatory reaction occurs by excessive neutrophil accumulation resulting in the damage to surrounding tissues. As inflammation mediators, there have been known G-CSF, GM-CSF, IFN-γ, IL-2, IL-6, etc. that are endogenous factors as well as LPS (lipopolysaccharide) that is derived from outside of the body.

Recently, numerous studies about LPC (lysophosphatidylcholine) and SPC (sphingosylphosphorylcholine) having LPA (lysophosphatidyl acid) or S1P (sphingosine 1-phosphate), which have been known as lipid transmitter, and a choline bound thereto, are being under progress. LPC and SPC have been known to have an important role in functioning not only as intermediates in biosynthesis of cellular membranes, together with LPA and SIP, but also as signaling molecules (Fukushima, N. et al., *Annu. Rev. Pharmacol. Toxicol.*, 41: 507-534, 2001). They are bound to their receptors and induce various cell reactions such as cell proliferation, differentiation, movement, cell death, etc. through several signal transductions (Lynch, K. R. et al., *Trends Pharmacol. Sci.*, 20(12): 473-475, 1999). The receptors to which they are bound are a kind of receptors that are classified as G protein-coupled receptors. Since OGR-1 (orphan G-protein-coupled receptor 1) was for the first time found as a receptor of SPC (Xu, Y. et al., *Nat. Cell. Biol.*, 2(5):264-267, 2000), studies about identifying ligands for GPR4- and G2A receptors having a structure similar to OGR-1 have been conducted. As a result, it was identified that GPR4 recognized SPC and LPC as its ligand and GPR4 promoted cell proliferation by SPC and LPC whereas OGR-1 suppressed cell proliferation by SPC (Zhu, K. et al., *J. Biol. Chem.*, 276(44): 41325-41335, 2001). Moreover, it was reported that G2A had a high affinity to LPC, however, it had a low affinity to SPC (Kabarowski, J. H. et al., *Science*, 293(5530): 702-705, 2001). G2A is mostly found in lymphocytes and the expression thereof is upregulated by stress and prolonged mitogenic signals. It was reported that in knockout mice that did not have G2A receptors, autoimmune diseases were caused (Le, L. Q. et al., *Immunity*, 14(5): 561-571, 2001).

Hence, in the course of conducting continuous studies to find out new therapeutic agents for treating inflammatory diseases, the present inventors identified that agonist ligands specific to G2A receptor that exists in neutrophils block suppression of neutrophil apoptosis by inflammation mediators and release of IL-8 (interleukin-8) in neutrophils and monocytes, and exhibit excellent therapeutic effect on an inflammatory disease, especially inflammatory diseases associated with hyperactivity of neutrophil and excessive release of IL-8, or a disease associated with microbial infection, and thus they have completed the present invention.

DETAILED DESCRIPTION OF THE INVENTION

Accordingly, it is an object of the present invention to provide a method for inducing neutrophil apoptosis in cells, tissues or a body using an agonist ligand specific to G2A receptor.

It is another object of the invention to provide a method for inhibiting the excessive release of IL-8 in cells, tissues or a body using an agonist ligand specific to G2A receptor.

It is further object of the invention to provide a method for increasing the bactericidal activity of neutrophils using an agonist ligand specific to G2A receptor.

It is still further object of the invention to provide a method for treating a disease or disorder associated with suppression of neutrophil apoptosis or excessive release of IL-8 using an agonist ligand specific to G2A receptor.

Further, it is another object of the invention to provide a pharmaceutical or therapeutical composition comprising an agonist ligand specific to G2A receptor as an active ingredient.

It is still another object of the invention to provide a novel therapeutic use of an agonist ligand specific to G2A receptor.

To achieve the object above, the present invention provides a method for inducing neutrophil apoptosis in cells, tissues or a body, comprising administering an agonist ligand specific to G2A receptor into the cells, tissues or body in an amount effective to induce neutrophil apoptosis.

To achieve another object of the invention, the invention provides a method for inhibiting release of IL-8 in cells, tissues or a body, comprising administering an agonist ligand specific to G2A receptor into the cells, tissues or body in an amount effective to inhibit release of IL-8.

To achieve another object of the invention, the invention provides a method for increasing bactericidal activity of neutrophils in cells, tissues or a body, comprising administering an agonist ligand specific to G2A receptor into the cells, tissues or body in an amount effective to increase bactericidal activity of neutrophils.

To achieve another object of the invention, the invention provides a method for treating or preventing a disease or disorder associated with suppression of neutrophil apoptosis or excessive release of IL-8 in a subject, comprising administering an agonist ligand specific to G2A receptor into the subject.

To achieve another object of the invention, the invention provides a pharmaceutical composition for inducing neutrophil apoptosis or inhibiting release of IL-8 comprising an agonist ligand specific to G2A receptor as an active ingredient.

To achieve another object of the invention, the invention provides a composition for treating or preventing a disease or disorder associated with suppression of neutrophil apoptosis or excessive release of IL-8 comprising an agonist ligand specific to G2A receptor as an active ingredient.

Further, to achieve another object of the invention, the invention provides a use of an agonist ligand specific to G2A receptor for the manufacture of a pharmaceutical composition for inducing neutrophil apoptosis or inhibiting release of IL-8 in cells, tissues or a body.

To achieve another object of the invention, the invention provides a use of an agonist ligand specific to G2A receptor for the manufacture of an agent for treating a disease or disorder associated with the suppression neutrophil apoptosis or excessive release of IL-8.

The present invention will be described in detail.

The agonist ligands specific to G2A receptor according to the present invention include LPC (lysophosphatidylcholine), SPC (sphingosylphosphorylcoline) and derivatives thereof.

The LPC as used herein is represented by the following formula I:

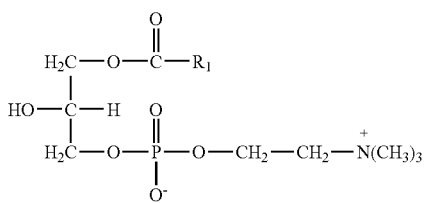

wherein $R_1$ is an alkyl Of $C_{4-30}$ or an alkenyl Of $C_{4-30}$ having one or more double bonds. Preferably, the LPC is not limited to, but may be selected from the group consisting of 1-stearoyl (18:0) lysophosphatidylcholine ($_{L-\alpha}$-Lysophosphatidylcholine stearoyl; Lysolecithin stearoyl), 1-oleoyl (18:1) lysophosphatidylcholine ($_{L-\alpha}$-Lysophosphatidylcholine oleoyl; Lysolecithin oleoyl), 1-myristoyl (14:0) lysophospatidylcholine ($_{L-\alpha}$-Lysophosphatidylcholine myristoyl), and 1-palmitoyl (16:0) lysophosphatidylcholine ($_{L-\alpha}$-Lysophosphatidylcholine palmitoyl; Lysolecithin palmitoyl; $_{DL-\alpha}$-Lysophosphatidylcholine palmitoyl).

Also, the SPC as used herein is represented by the following formula II:

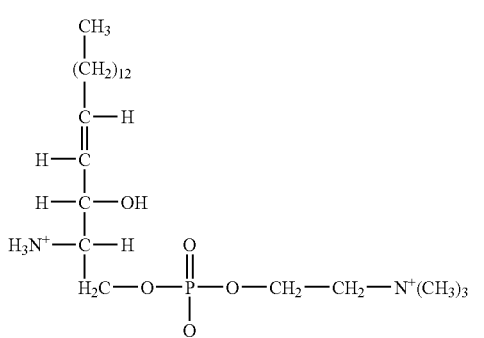

In the SPC of the above formula II, the number of terminal carbons in the sphingosine portion may be from 4 to 30.

Further, in the present invention, the derivatives of LPC or SPC may be used. Preferably, they may be ether derivatives of LPC represented by the following formula III:

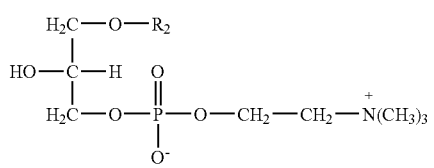

wherein $R_2$ is an alkyl of $C_{4-30}$ or an alkenyl of $C_{4-30}$ having one or more double bonds. More preferably, they are not limited to, but may be selected from the group consisting of $_{L-\alpha}$-lysophosphatidylcholine-$_\gamma$-O-alk-1-enyl (Lysophosphatidalcholine), $_{L-\alpha}$-lysophosphatidylcholine-$_\gamma$-O-alkyl (Lyso-platelet activating factor), $_{DL-\alpha}$-lysophosphatidylcholine-$_\gamma$-O-hexadecyl (rac-Lyso-platelet activating factor), and $_{L-\alpha}$-lysophosphatidylcholine-$_\gamma$-O-hexadecyl (Lyso-platelet activating factor; Lyso-PAF-$C_{16}$).

The LPC, SPC and derivatives thereof are commercially available with ease. Specifically, they can be purchased from Sigma Chemical Co. (USA). Further, they may be isolated from animals and also can be prepared according to synthetic methods well known in the pertinent art. The LPC, SPC and derivatives thereof are endogenous substances in mammal, and thus their safety is as good as proven.

The agonist ligands specific to G2A receptor according to the present invention largely show two activities. First, they do not show in vitro direct antibacterial effect but have in vivo functions of blocking both suppressed apoptosis of neutrophils and release of IL-8 in neutrophils and monocytes. Therefore, they can be effectively used in treatment or prevention of a disease or disorder associated with suppression of neutrophil apoptosis and/or excessive release of IL-8.

Second, the agonist ligands specific to G2A receptor according to the present invention enable neutrophils to kill pathogens more readily by increasing their bactericidal ability. In this respect, the agonist ligands according to the invention can be said as a new type of antibacterial agent because they do not show direct killing effects against pathogens but enable neutrophils to eliminate pathogens more readily. Therefore, the agonist ligands according to the invention can be used as a therapeutic agent or therapeutic additive for various diseases associated with microbial infection.

The pharmaceutical composition, or therapeutic or preventive composition comprising an agonist ligand specific to G2A receptor according to the invention may further comprise pharmaceutically acceptable carriers, for example, carriers for oral administration or for parenteral administration. The carriers for oral administration may include lactose, starch, cellulose derivatives, magnesium stearate, stearic acid and so on. For oral administration, the agonist ligands specific to G2A receptor according to the invention can be used in the form of intake-type tablets, buccal tablets, troches, capsules, elixirs, suspensions, syrups, wafers, etc. in an admixture of excipients. Also, the carriers for parenteral administration may comprise water, suitable oils, salines, water-soluble glucose and glycols, etc, and may further comprise stabilizer or preserver. As a suitable stabilizer, there are antioxidants such as ascorbic acid, sodium sulfite or sodium hydrogen sulfite. As a suitable preserver, there are benzalkonium chloride, methyl- or propyl-paraben and chlorobutanol. For other pharmaceutically acceptable carriers, the following literature can be consulted: Remington's Pharmaceutical Sciences, 19th ed., Mack Publishing Company, Easton, Pa., 1995.

The pharmaceutical composition or therapeutical composition according to the present invention can be formulated into various parenteral or oral dosage forms. Typical dosage form for parenteral administration is a dosage form for injection, preferably, an isotonic aqueous solution or a suspension. The dosage form for injection can be prepared using suitable dispersion agent, wetting agent or suspension agent according to the known methods in the pertinent art. For example, each ingredient is dissolved in saline or buffer, and then can be formulated into a dosage form for injection. Also, typical dosage form for oral administration is tablets, capsules, etc., which may comprise diluents (Ex.: lactose, dextrose, sucrose, mannitol, sorbitol, cellulose and/or glycine), or lubricants (Ex.: silica, talc, stearic acid and magnesium or calcium salt thereof and/or polyethylene glycol) in addition to the active ingredient. Furthermore, the tablets may further comprise binders such as magnesium aluminum silicate, starch paste, gelatin, tragacanth, methylcellulose, sodium carboxymethylcellulose and/or polyvinylpyrrolidine. If necessary, they may further comprise disintegrants or effervescent mixtures such as starch, agar, alginic acid or sodium salt thereof, and/or absorbents, colorants, flavors and sweeteners. Such dosage form can be prepared by conventional mixing, granulation or coating methods.

The pharmaceutical composition or therapeutic composition of the present invention may comprise additives such as antiseptics, hydrates or emulsion accelerators, salts for the regulation of osmotic pressure and/or auxiliary such as buffers, and other therapeutically useful substances. It can be prepared as formulations according to conventional methods.

The agonist ligands specific to G2A receptor as an active ingredient of the pharmaceutical composition or therapeutical composition of the present invention can be administered into mammals including humans via parenteral or oral route in an amount of 0.01 to 100 mg/kg (body weight) once or several times a day. The extent of administered amount may vary suitably by the age, body weight, health condition, sex, the degree of disease, diet, administration time, excretion rate, administration route and so on. The pharmaceutical composition or therapeutic composition of the invention is not restricted to special dosage, administration route and administration method as far as it retains the inventive effects. Furthermore, the agonist ligands specific to G2A receptor according to the present invention may be co-administered together with antibiotics or therapeutic agents for inflammation that are generally used for inflammation diseases when applied to inflammatory diseases, and co-administered together with various antibacterial agents comprising the previous antibiotics when applied to treat a disease associated with microbial infection.

The agonist ligands specific to G2A receptor according to the present invention can be effectively used for the treatment of a disease or disorder associated with neutrophil accumulation due to suppression of apoptosis and neutrophil hyperactivity and/or the excessive release of IL-8, especially inflammatory diseases. The inflammatory diseases to which the agonist ligands according the present invention can be applied include all of the acute or chronic inflammatory diseases associated with suppression of neutrophil apoptosis and hyperactivity of neutrophil and/or the excessive release of IL-8, and complication thereof. The 'chronic inflammation' refers to all diseases that induce tissue injury or induce continuous inflammation due to excessive neutrophil accumulation and hyperactivity and the excessive release of IL-8, and complication thereof. In particular, the inflammatory diseases to which the agonist ligands of the invention can be applied are not limited to, but include inflammatory bowel disease such as Crohn's disease and ulcerative colitis, peritonitis, osteomyelitis, cellulitis, meningitis, cerebritis, pancreatitis, trauma-inducing shock, bronchial asthma, allergic rhinitis, cystic fibrosis, cerebral apoplexy, acute bronchitis, chronic bronchitis, acute bronchiolitis, chronic bronchiolitis, osteoarthritis, gout, spinal arthropathy, ankylosing spondylitis, Reiter's syndrome, psoriatic arthropathy, enteropathic spondylitis, juvenile arthropathy, juvenile ankylosing spondylitis, reactive arthropathy, infectious arthritis, post-infectious arthritis, gonococcal arthritis, tuberculous arthritis, viral arthritis, fungal arthritis, syphilitic arthritis, Lyme disease, arthritis associated with 'vasculitis syndrome', polyarteritis nodosa, hypersensitivity vasculitis, Wegener's granulomatosis, polymyalgia rheumatica, giant cell arteritis, calcium crystal deposition arthropathy, pseudogout, non-joint rheumatism, bursitis, tenosynovitis, epicondylitis (tennis elbow), neuropathic joint disease(charcot joint), hemarthrosic, Henoch-Schonlein purpura, hypertrophic osteoarthropathy, multicentric reticulohistiocytoma, scoliosis, hemochromoatosis, meniscocytosis, other hemoglobinopathy, hyperlipoproteinemia, hypogammaglobulinaemia, familial mediterranean fever, Gerhardt Disease, systemic lupus erythematosus, relapsing fever, psoriasis, multiple sclerosis, sepsis (septicemia), septic shock, acute respiratory distress syndrome, multiple organ dysfunction syndrome, chronic obstructive pulmonary disease, rheumatic arthritis, acute lung injury, bronchopulmonary dysplasia and so on.

In addition, it was reported that in patients with ischemia-reperfusion injury, neutrophils was excessively accumulated. That is, almost all the organs and tissues including heart, brain, kidney, liver, etc. are subject to tissue damages owing to reperfusion when the disorder of blood stream occurs. It has been known that the neutrophil has an important role in this process (Jordan et al., Cardiovasc. Res., 43, 860-78, 1999). Accordingly, the agonist ligands according to the present invention can be applied to treat ischemia-reperfusion injury including ischemic brain disease, ischemic heart disease, ischemic kidney disease, ischemic liver disease, ischemic bowel disease, organ injury due to the disorder of blood stream in transplantation, etc. as well as inflammatory diseases.

Further, the present invention provides a therapeutic use of the agonist ligands specific to G2A receptor. Specifically, the present invention provides a use of the agonist ligands specific to G2A receptor for the manufacture of a pharmaceutical composition for recovering the suppressed apoptosis of neutrophils, inhibiting release of IL-8, or increasing the bactericidal activity of neutrophils, in cells, tissues or a body. The pharmaceutical composition may further comprise pharmaceutically acceptable carriers in addition to LPC (formula I), SPC (formula II) or derivatives thereof, preferably ether derivatives of LPC (formula III). The examples of the pharmaceutical acceptable carriers are as listed above. The pharmaceutical composition according to the present invention can be administered orally or parenterally, and the examples of the oral or parenteral administration are as mentioned above. Also, the present invention provides a use of the agonist ligands specific to G2A receptor for the manufacture of an agent for treating a disease or disorder associated with suppression of neutrophil apoptosis and hyperactivity of neutrophil and/or excessive release of IL-8. The examples of diseases or disorders to which the agonist ligands according to present invention can be applied are as listed above.

RT(+): RT-PCR is performed with reverse transcriptase.

RT(−): RT-PCR is performed without reverse transcriptase (Control group)

Figure 4:
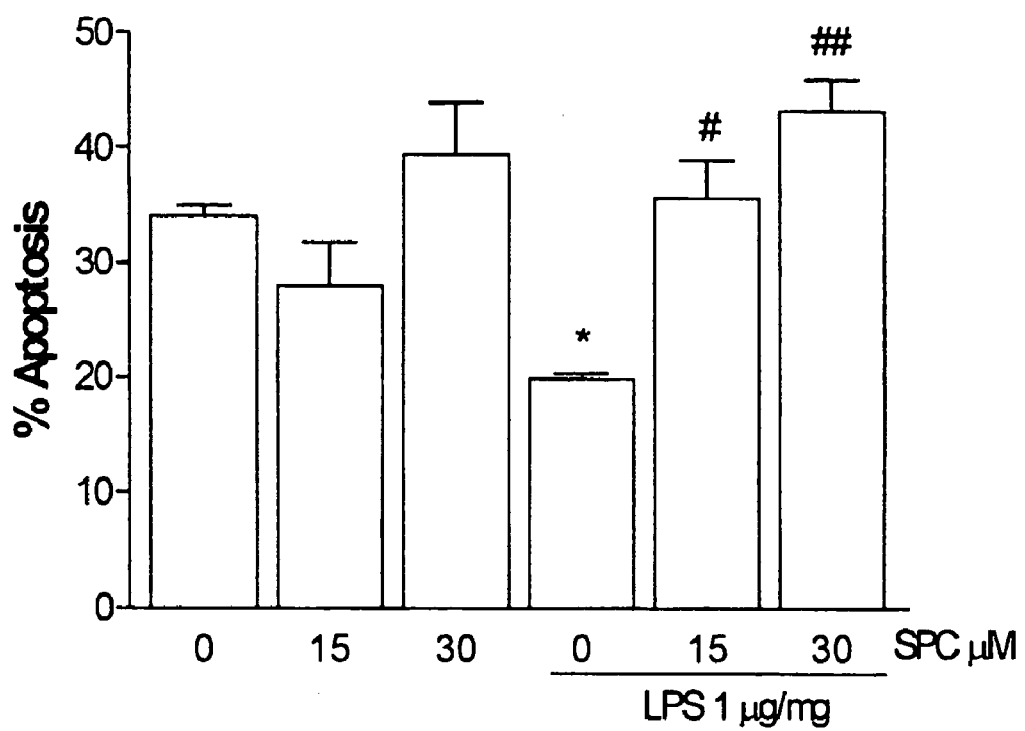

FIG. 4 shows the inhibitory effects of SPC against suppression of neutrophil apoptosis that is induced by LPS.

Figure 5:
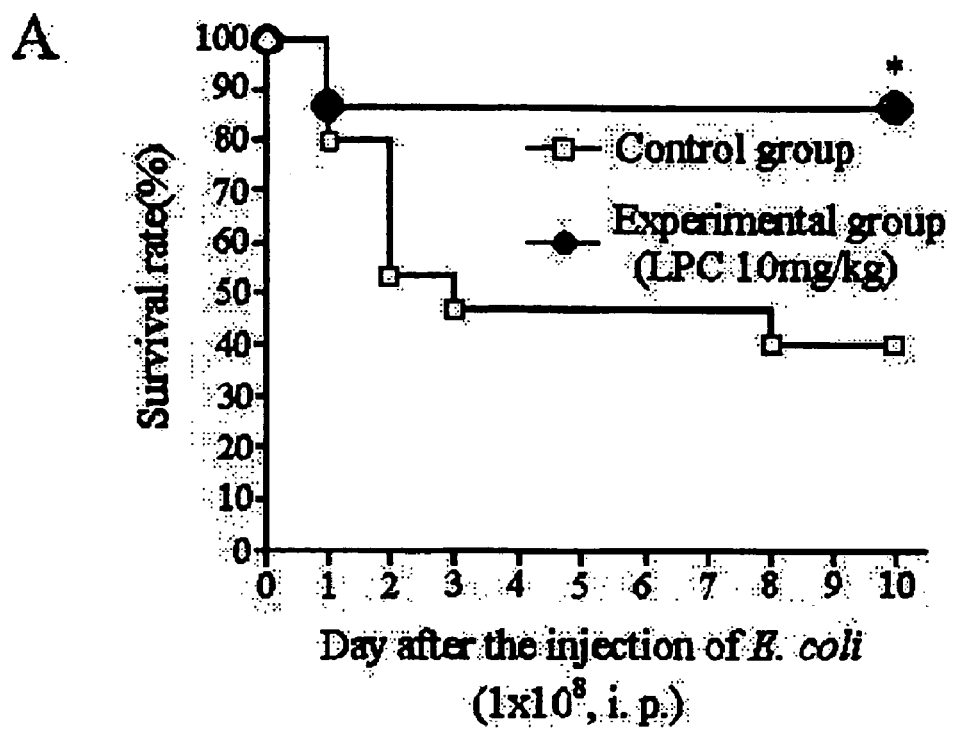
Figure 5:
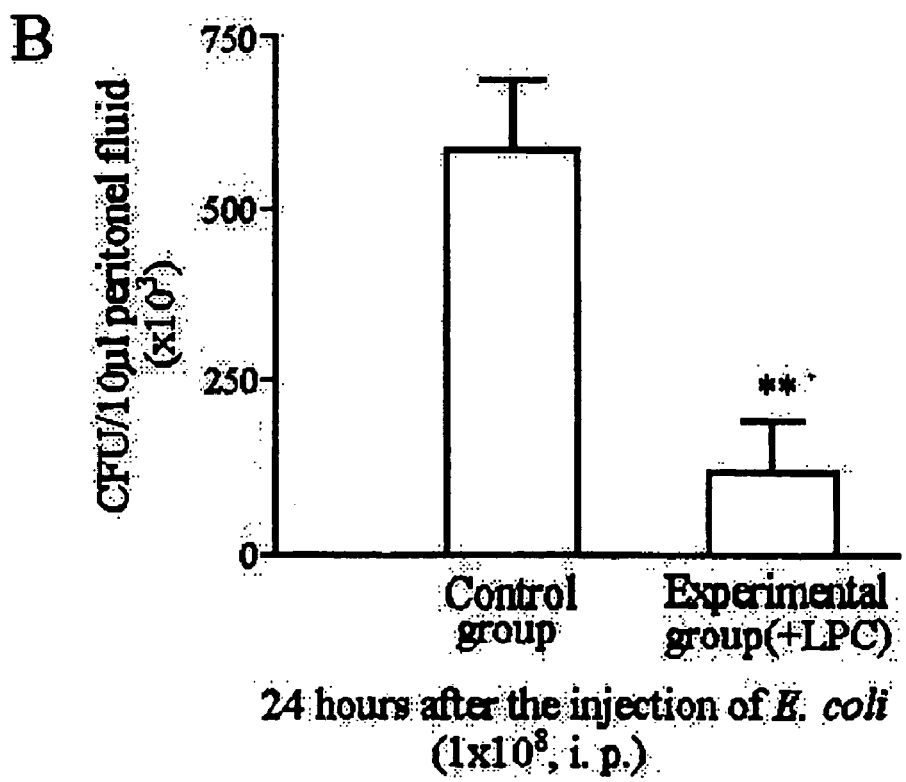

FIG. 5 shows the effects of 1-stearoyl LPC in *E. coli*-induced septicemia model.

A: The survival rate of mice as time lapses after the administration of LPC

Figure 6:
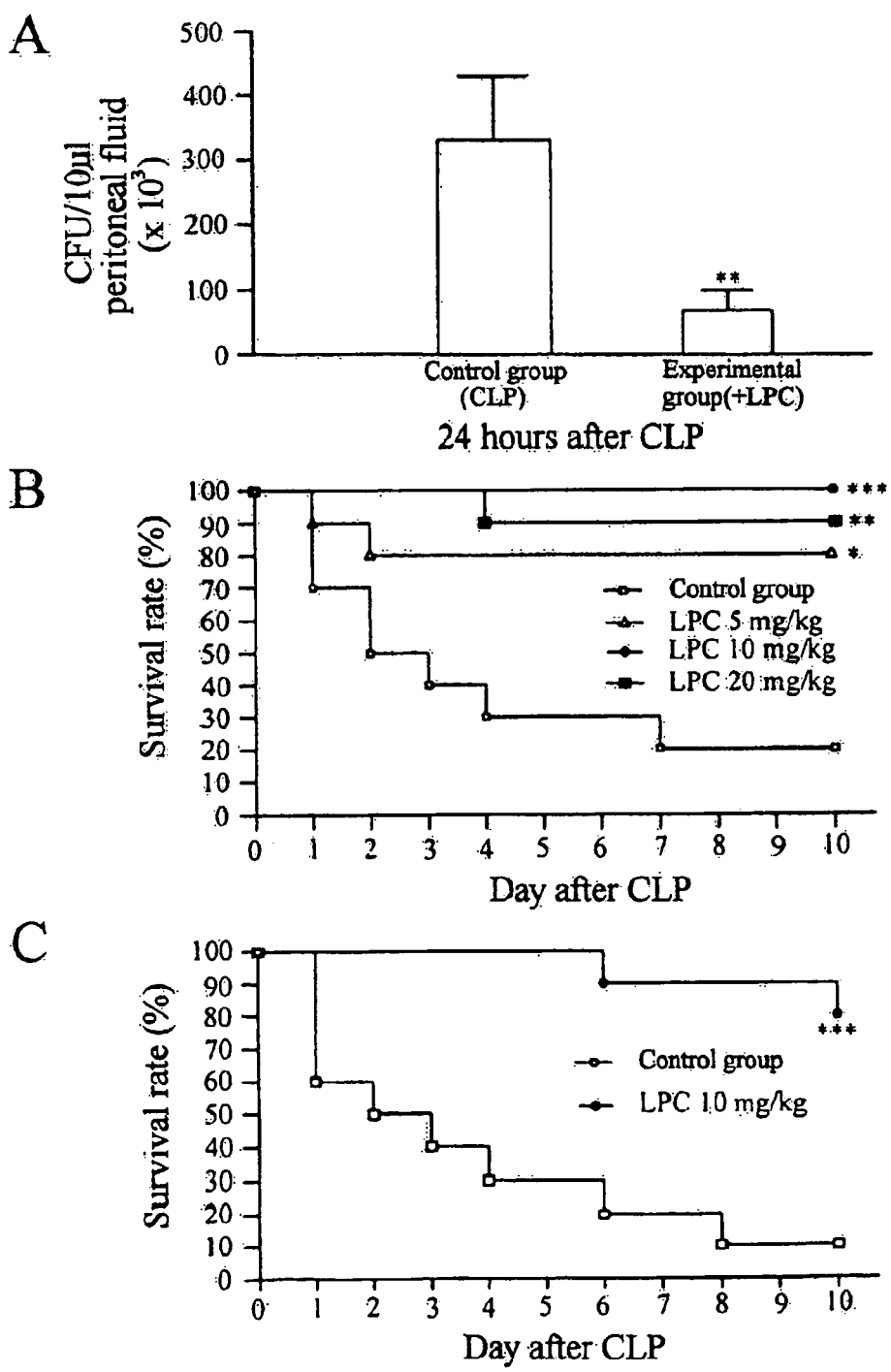

B: The number of intraperitoneal *E. coli* cells in mice 24 hours after LPC is administered FIG. 6 shows the effects of 1-steroyl LPC in CLP-induced septicemia model.

A: The numbers of intraperitoneal *E. coli* cells in mice when LPC is administered 2 hours and 14 hours after the CLP surgery, respectively B: The survival rates of mice as time lapse when LPC is administered four times at intervals of 12 hours, 2 hours after the CLP surgery C: The survival rates of mice as time lapse when LPC is administered four times at intervals of 12 hours, 10 hours after the CLP surgery.

Figure 7:
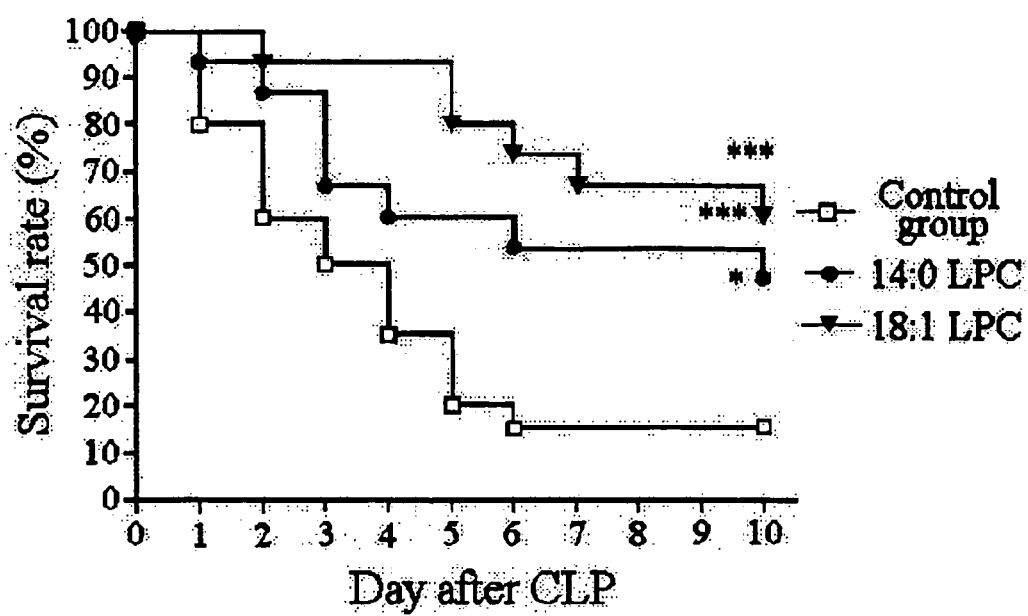

FIG. 7 shows the effects of 1-myristoyl LPC (14:0 LPC) and 1-oleoyl LPC (18:1 LPC) in CLP-induced septicemia model.

Figure 8:
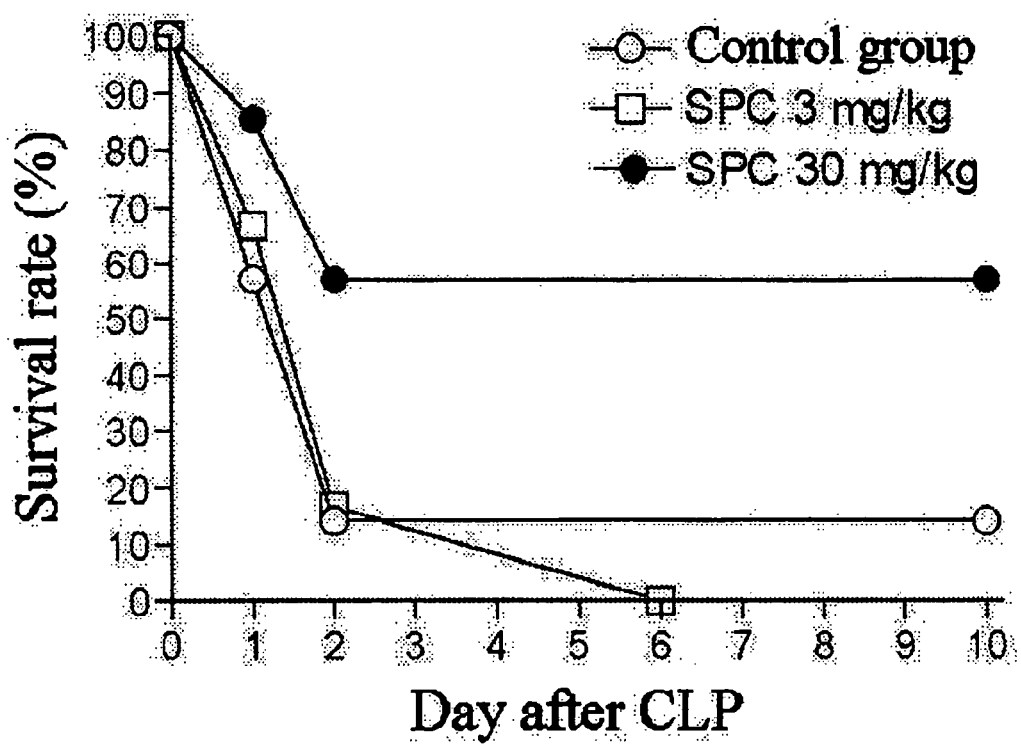

FIG. 8 shows the effects of SPC in CLP-induced septicemia model.

Figure 9:
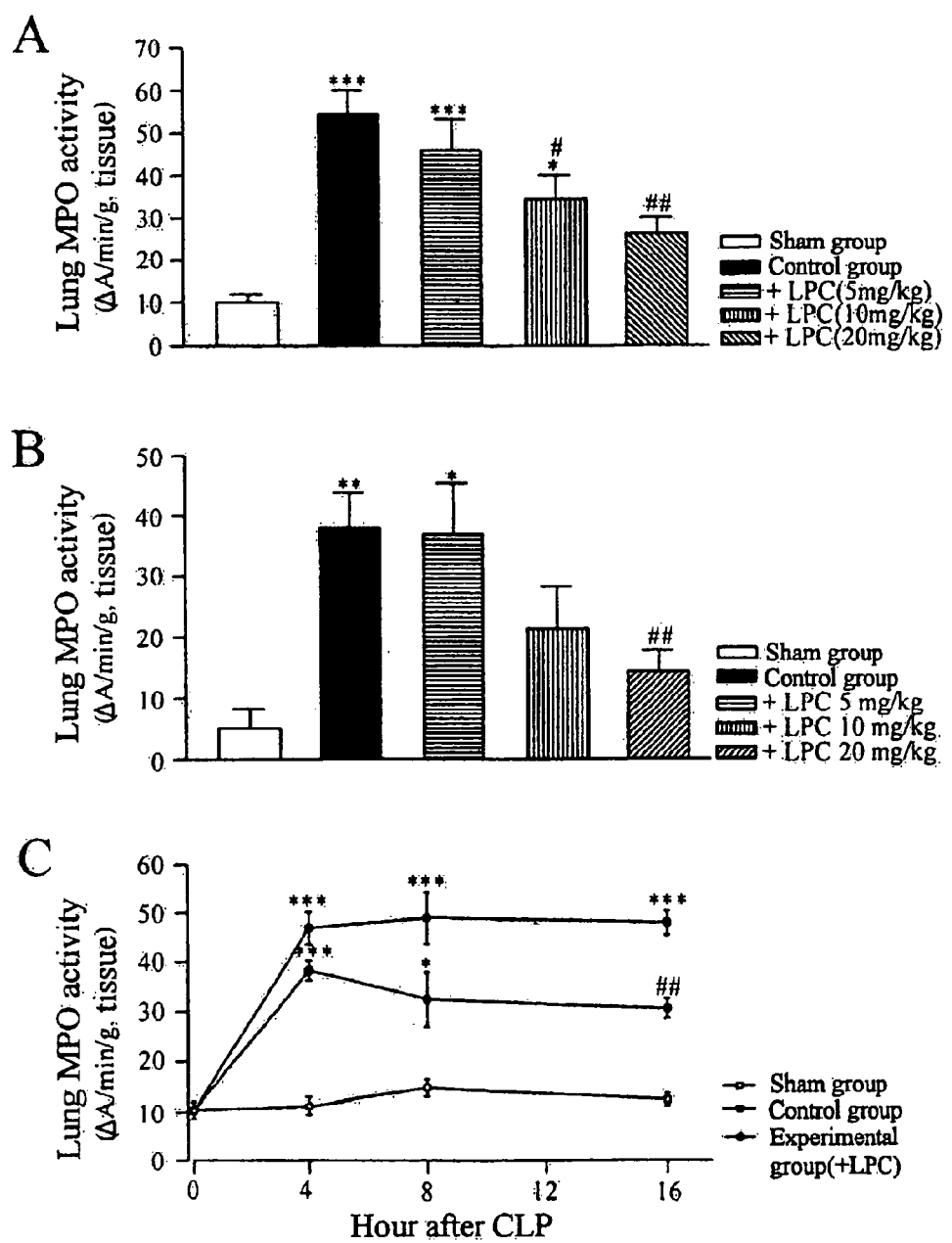

FIG. 9 shows the effects of 1-stearoyl LPC against acute respiratory distress syndrome in local LPS-induced acute lung injury model (A), systemic LPS-induced acute lung injury model (B) and acute lung injury model by CLP-induced sepsis (C).

Figure 10:
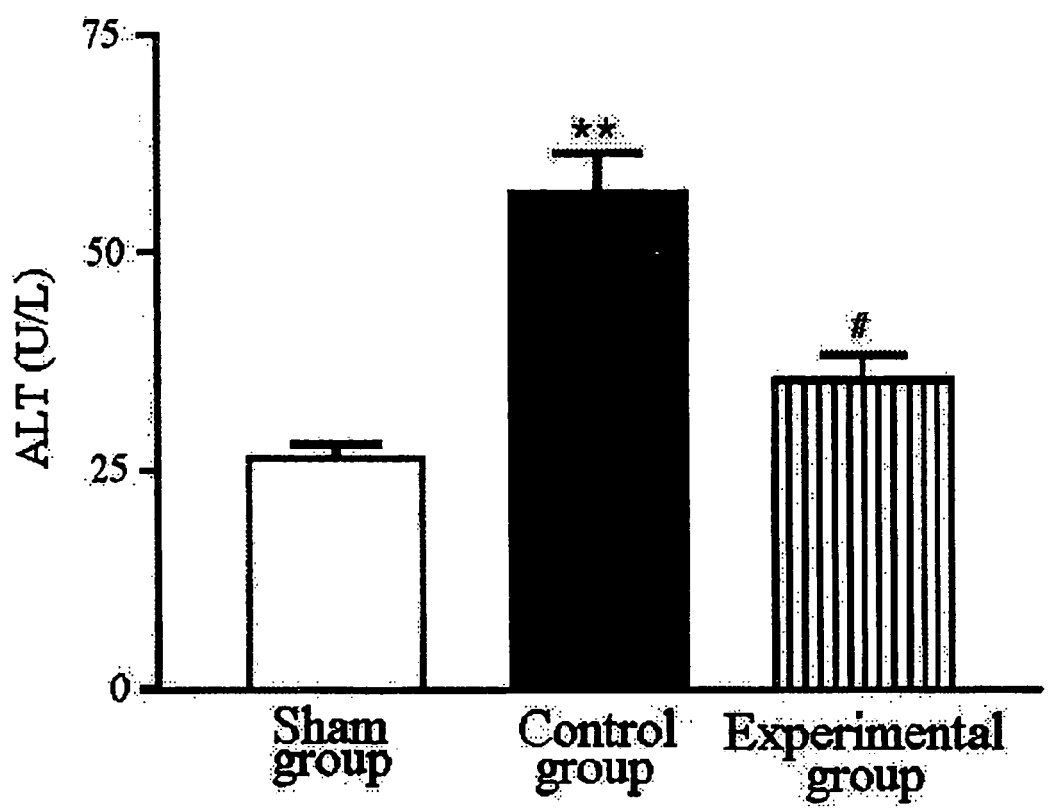

FIG. 10 shows the effects of 1-stearoyl LPC against multiple organ dysfunction syndrome in CLP-induced sepsis model.

Figure 11:
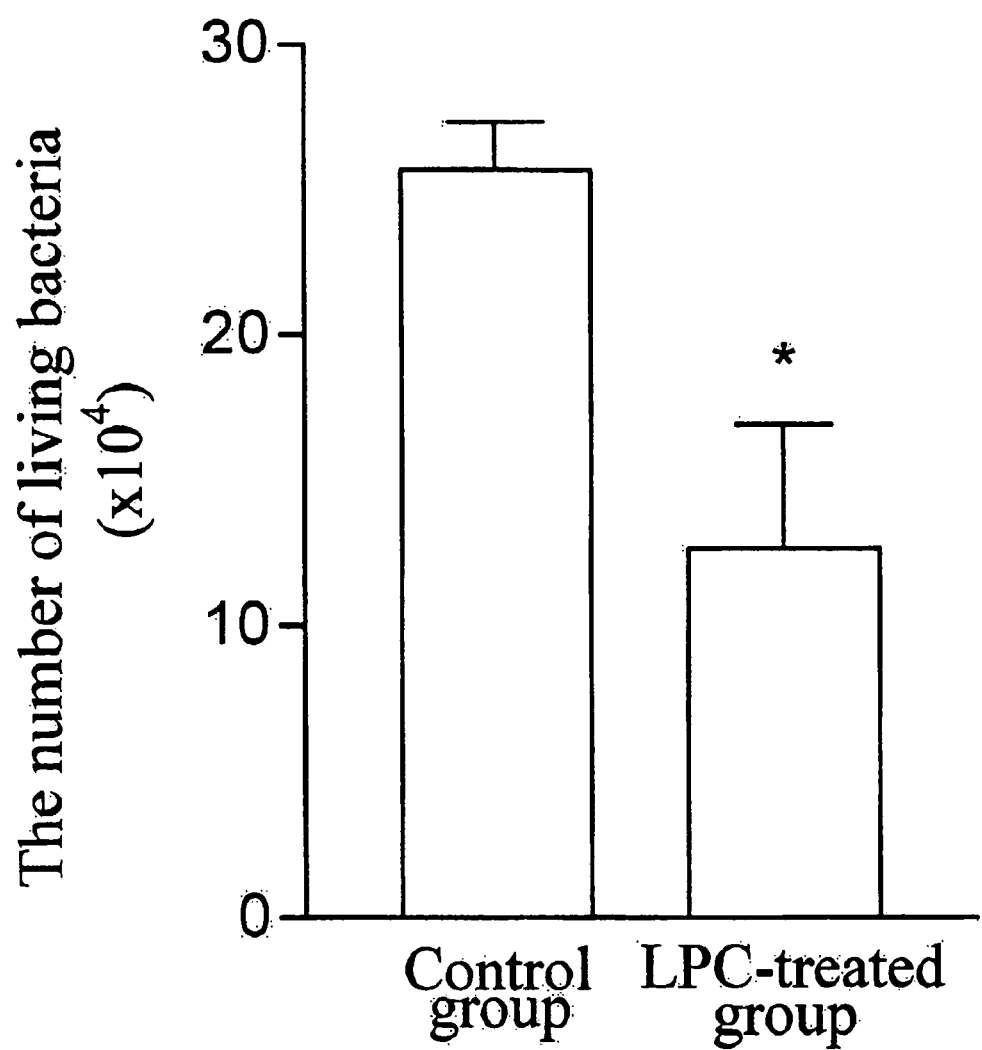

FIG. 11 shows the effects of 1-stearoyl LPC regarding bactericidal activity of neutrophils in bacteria-induced sepsis model.

BEST MODE FOR CARRYING OUT THE INVENTION

The present invention will be described by virtue of the following examples in more detail.

However, the examples shown below are provided solely to illustrate the invention; the scope of the invention should not be construed to be limited thereto. In the following examples, percentages with regard to solid/solid mixture, liquid/liquid, and liquid/solid are based on weight/weight, volume/volume, and weight/volume, respectively, and all reactions were carried out at room temperature unless indicated otherwise.

EXAMPLE 1

Inhibitory Effects of LPC against Anti-apoptosis of Neutrophils by Inflammation Mediators <1-1> Isolation of Neutrophils Neutrophils were isolated from healthy adults using discontinuous percoll gradient according to the method of Szucs, S. et al. (*J. Immunol. Methods*, 167: 245-251, 1994). First, plasmas were separated from heparinized whole blood, and red blood cells were depleted by dextran sedimentation. Thereafter, leukocytes were layered over a percoll gradient with densities of 1.077 and 1.094 (Pharmacia, Sweden). Separated neutrophil layers were recovered from the percoll gradient interface, and then washed with HBSS (Hank's balanced salt solution, Sigma Chemical Co., USA). The remaining pellet was resuspended in RPMI 1640 medium supplemented with 10% FBS (fetal bovine serum) and 2 mM gentamicin. As a result of the examination of the cytospin stained with Wright-Giemsa (Sigma Chemical Co., USA), it was observed that the resuspension solution contained 95% or more neutrophils. Also, as a result of examination using trypan blue dye exclusion method, 98% or more neutrophils were observed.

Figure 1:
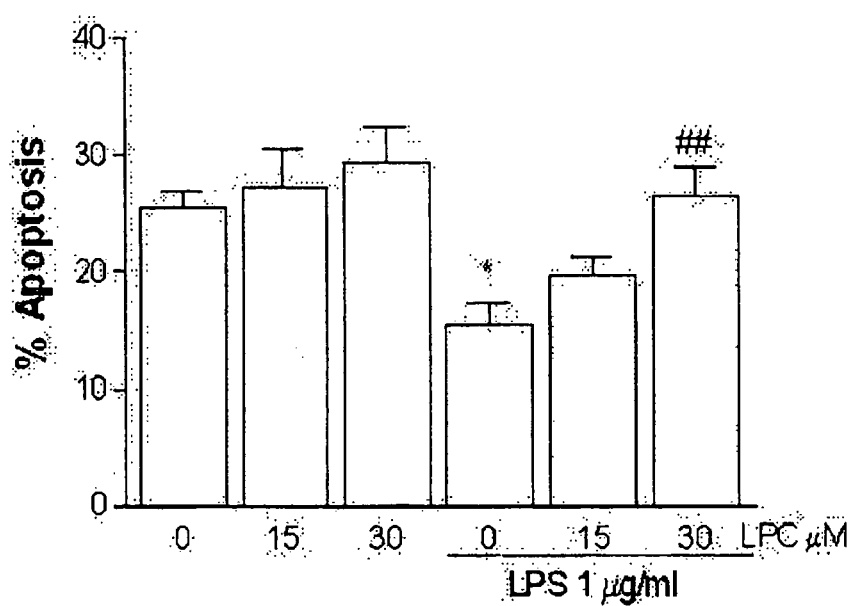
FIG. 1 shows the inhibitory effects of 1-stearoyl LPC against suppression of neutrophil apoptosis that is induced by an exogenous inflammation mediator (LPS; A) or endogenous inflammation mediators (GM-CSF, G-CSF and IFN-γ; B).
Figure 1:
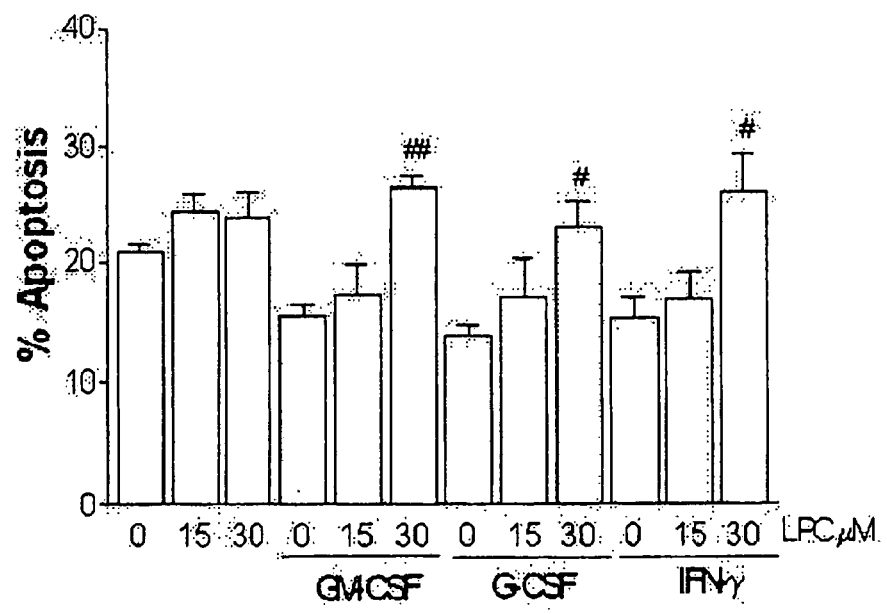

<1-2> Inhibitory Effects of LPC Against Anti-Apoptosis of Neutrophils by Exogenous Inflammation Mediator $1 \times 10^5$ neutrophil cells isolated in above Example <1-1> were cultured in a 96-well plate to which RPMI1640 medium containing 10% FBS was added. Thereafter, they were treated with 1-stearoyl lysophosphatidylcoline (Sigma Chemical Co., USA) in concentrations of 15 μM and 30 μM, respectively. After 1 hour, they were treated with 1 μg/ml LPS (Sigma Chemical Co.). After 24 hours, the medium was removed from the plats, and the remaining cells were washed twice with PBS (phosphate-buffered saline) buffer at 4° C. The cells adhered to the bottom of the plate were all scraped and put into a 1.5-ml eppendorf tube. Then, they were centrifuged at 2500 rpm for 5 min, and the supernatant was removed. Again, 0.1 ml of PBS buffer at 4° C. was added to the pellet, which was then well mixed using pipetting. To 25 μl of the cell suspension was added 2 μl of AcOr/EtBr dye solution in which 100 μg/ml of acridine orange (AcOr) and 100 μg/ml of ethidium bromide (EtBr) were mixed. Then, the percentage of apoptotic cells/total cells was calculated with observing the neutrophil cells under a fluorescence microscope. As a result, as shown in FIG. 1A, the percentage of neutrophil apoptosis that had been decreased by LPS was increased by 1-stearoyl LPC in a concentration-dependent manner. Accordingly, it can be seen that LPC effectively blocks the effect of exogenous inflammation mediator that inhibits neutrophil apoptosis.

<1-3> Inhibitory Effects of LPC Against Anti-Apoptosis of Neutrophils by Endogenous Inflammation Mediators The experiments were carried out according to the same methods as used in Example <1-2> except that the neutrophils isolated in Example <1-1> were treated with 100 ng/ml GM-CSF (Sigma Chemical Co.), 100 ng/ml G-CSF (Sigma Chemical Co.) and 100 ng/ml IFN-γ (Sigma Chemical Co.), respectively, instead of LPS. As a result, as shown in FIG. 1B, the percentage of neutrophil apoptosis that had been decreased by endogenous inflammation mediators was increased by 1-stearoyl LPC in a concentration-dependent manner. Accordingly, it can be seen that LPC effectively blocks the inhibitory effects of neutrophil apoptosis by endogenous inflammation mediators as well as exogenous inflammation mediators.

EXAMPLE 2

Inhibitory Effects of LPC against Release of IL-8, which is an Inflammation-Inducing Cytokine Regarding release of IL-8, an important inflammation-inducing cytokine in neutrophils and blood monocytes, which is seriously considered in onset mechanism of inflammatory diseases, the effects of LPC were investigated.

<2-1> Isolation of Neutrophils

Neutrophils were isolated according to the method of Szucs, S. et al. (*J. Immunol. Methods*, 167: 245-251, 1994) as described in above Example <1-1>.

<2-2> Isolation of Monocytes

Peripheral bloods were collected from a healthy person, put into a heparinized tube and then well mixed with 1× PBS buffer. Then, they were layered in Ficoll-Hypaque solution (density 1.077, Sigma Chemical Co., USA) and then centrifuged at 2500 rpm at 4° C. for 25 min. After the monocyte layer between Ficoll layer and plasma layer had been cautiously recovered, 1×PBS buffer was added thereto and mixed well. It was then centrifuged again at 2500 rpm at 4° C. for 25 min. Such centrifugation procedures were repeated twice until red blood cells were depleted. Thereafter, the pellet was cultured in FBS at 37° C. for 15 min and centrifuged at 2500 rpm for 10 min. Then, 1×PBS buffer was added again to the pellet. The isolated cells were layered in percoll solution (density 1.066) and then centrifuged at 2500 rpm at 4° C. for 30 min. After only monocyte layer had been recovered from the isolated layers, 1×PBS buffer was added thereto. They were centrifuged at 2500 rpm for 15 min. After the centrifugation had been repeated twice or three times, the isolated monocytes were inoculated into RPMI1640 medium containing 10% FBS and cultured in an incubator of 5% $CO_2$ at 37° C.

<2-3> Measurement of IL-8

Figure 2:
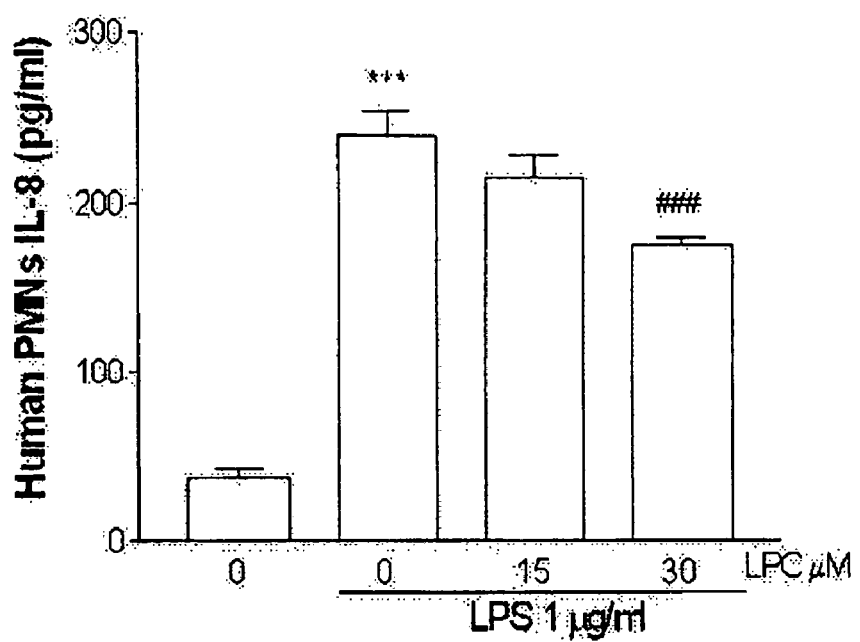
FIG. 2 shows the inhibitory effects of 1-stearoyl LPC against the excessive release of IL-8 that is induced by LPS in neutrophils (A) and monocytes (B).
Figure 2:
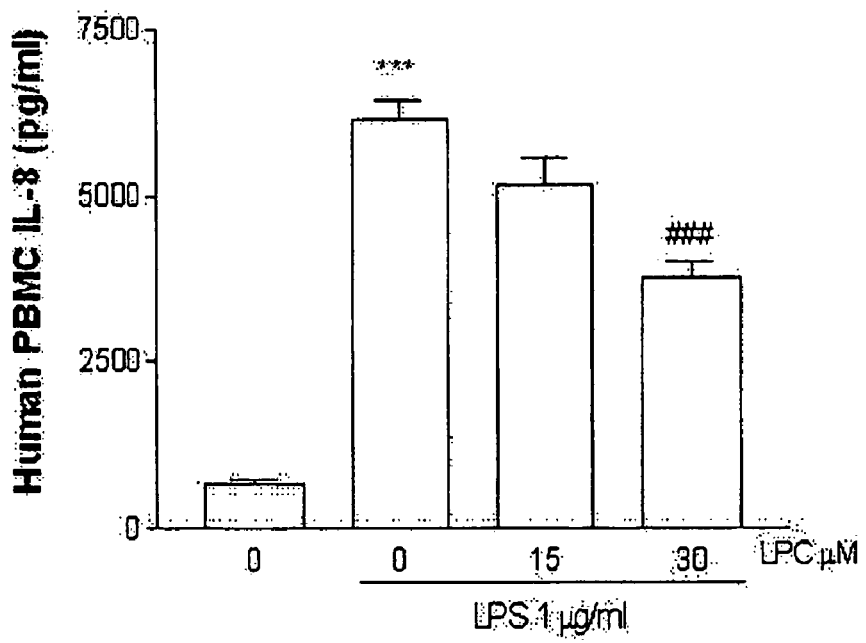

The neutrophils and monocytes isolated in Examples <2-1> and <2-2> above were cultured in a 96-well plate to which RPMI1640 medium containing 10% FBS was added, at a concentration of $1 \times 10^5$ cells/well/0.2 ml, respectively. They were treated with 1-stearoyl LPC at concentrations of 15 μM and 30 μM, respectively. After 1 hour, they were treated with 1 μg/ml LPS. After 3 hours, supernatants were collected and put into an eppendorf tube. Then, the level of IL-8 was measured using ELISA kit (Biosource, USA). As a result, as shown in FIG. 2, the level of IL-8 release that had been increased by LPS in neutrophils (A; human PMNs) and monocytes (B; human PBMC) was inhibited by LPC in a concentration-dependent manner.

EXAMPLE 3

Search for LPC-Specific Receptors that Exist in Neutrophils

Until now, G2A and GPR4 have been known as receptors to which LPC specifically binds (Zhu, K. et al., *J. Biol. Chem.*, 276(44): 41325-41335, 2001; Kabarowski, J. H. et al., *Science*, 293(5530): 702-705, 2001). Especially, the fact that G2A exists in monocytes as a receptor of LPC was reported by Rikitake et al. (Rikitake et al., *Arterioscler Thromb Vasc Bio.l*, 22: 2049-53, 2002). However, in neutrophils, nothing has been known. Accordingly, the present inventors investigated whether LPC-specific receptors are in neutrophils.

Figure 3:
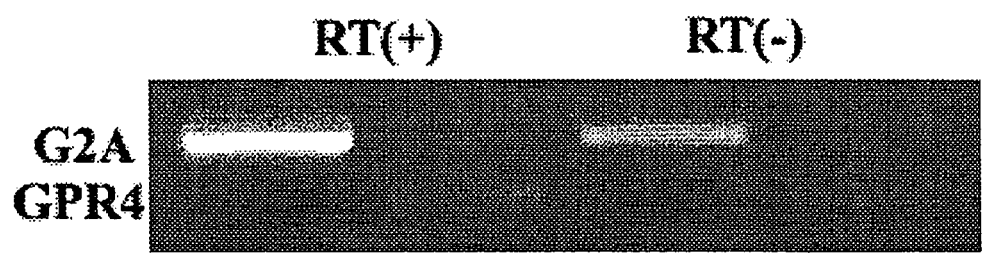
FIG. 3 shows the RT-PCR results obtained using RNA isolated from neutrophils as a template and primers specific to G2A- or GPR4 receptors.

First, neutrophils were isolated from human bloods according to the same methods in above Example <1-1>. RNA was then isolated from the isolated neutrophils using TRIZOL reagent (GibcoBRL, USA). RT-PCR was carried out using primers specific to G2A (SEQ ID NO: 1 and SEQ ID NO:2) and primers specific to GPR4 (SEQ ID NO: 3 and SEQ ID NO: 4), respectively. The sizes of G2A and GRP4 to be amplified by each primer were 409 bp and 247 bp, respectively. The PCR condition was as follows: 40 cycles of 94° C./2 min, 60° C./1.5 min and 72° C./2 min. As a control, RT-PCR was carried out without reverse transcriptase (RT). As a result, as shown in FIG. 3, the expression level of G2A was remarkably increased as compared with the control group. On the other hand, the expression level of GPR4 showed no difference from that of the control group. The expression of each receptor observed in the control group is regarded as being due to the fact that DNA was completely not removed during the RNA isolation process. From these experiment results, it is considered that LPC does have inhibitory function of anti-apoptosis and inhibit release of IL-8 by acting upon G2A receptor.

EXAMPLE 4

Inhibitory Effects of SPC against Anti-apoptosis of Neutrophils by Inflammation Mediators In order to examine whether SPC, known as another agonist ligand for G2A receptor, does have the same functions as LPC, experiments were carried out according to the same methods as used in above Example <1-2> except that instead of LPC, SPC (Sigma-Aldrich Co.) was used. The results were shown in FIG. 4. As shown in FIG. 4, the percentage of neutrophil apoptosis that had been decreased by LPS was increased by SPC in a concentration-dependent manner. Accordingly, it can be seen that SPC, another ligand specific to G2A receptor, has the same functions as LPC.

REFERENCE EXAMPLE 1

Preparation of Septicemia Model

<1-1> Directly Induced Sepsis Model: Bacteria-induced Sepsis Model & LPS-induced Sepsis Model a) Bacteria-Induced Sepsis Model ICR mice (25-30 g in body weight; MJ Ltd.) were intraperitoneally injected with alive $10^8$ cells/ml *E. coli* (DH5a) that were suspended in 0.5 ml of PBS (phosphate-buffered saline) to cause peritonitis, thereby inducing sepsis.

b) LPS-Induced Sepsis Model

ICR mice (25-30 g in body weight; MJ Ltd.) were intraperitoneally injected with LPS (induced from *E. coli* 055:B5) in an amount of 1 mg/kg thereby inducing Sepsis.

<1-2> Indirectly Induced Sepsis Model: CLP-Induced Sepsis Model

After ICR mice (25-30 g in body weight; MJ Ltd.) had been anesthetized with pentobarbital, right abdominal sites of the mice were dissected in a length of 1 cm to expose their cecum, and sites below the ileocecal valve were ligated. And then, after 4~6 punctures had been created on the cecum with 21-gauge needle, the abdomen was sutured again to cause peritonitis, thereby inducing Sepsis.

REFERENCE EXAMPLE 2

Determination of the Activity of Myeloperoxidase in Pulmonary Tissues

The activity of myeloperoxidase (MPO), an indicator of neutrophils, in pulmonary tissues was determined according to the methods of Goldblum et al (*J. Appl. physiol.* 59: 1978, 1985) and Parey et al (*J. Immunol.* 160:1007, 1998). First, mice were sacrificed and pulmonary tissues were obtained therefrom. The tissues had been homogenized in potassium phosphate buffer, and centrifuged to obtain pellets. These pellets were sonicated in potassium phosphate buffer containing 0.5% hexadecyltrimethylammonium bromide (HTAB), and incubated at 60° C. for 120 min. After centrifugation, supernatants were obtained. 0.02 ml of supernatants was mixed with potassium phosphate buffer solution (0.18 ml) containing o-dianisidine dihydrochloride of 0.167 mg/ml and 0.0005% hydrogen peroxide. Accordingly, the absorbance of the mixture was determined at a wavelength of 460 nm.

REFERENCE EXAMPLE 3

Determination of the Number of Intraperitoneal *E. coli*

After the peritoneal cavity of mice had been exposed, it was washed with sterilized saline (2 ml). The resultant solution was diluted with HBSS (Sigma Chemical Co., USA) in a ratio of 1/1000, and then 10 μl of each diluted solution was spread on Trypticase Soy agar (BBL, Becton Dickinson Co., USA) plates. After overnight incubation at 37° C., colony forming unit (CFU) was measured.

EXAMPLE 5

Therapeutic Effects of 1-Stearoyl LPC in Bacteria-Induced Sepsis Model

14 ICR mice of bacteria-induced septicemia model according to Reference Example <1-1> a) were divided into two groups of 7 mice. 7 mice were administered with 1-stearoyl LPC (Sigma Chemical Co., USA) dissolved in 1% BSA (bovine serum albumin) solution containing no fatty acid in an amount of 10 mg/kg by subcutaneous injection, 2 and 14 hours after *E. coli* was intraperitoneally injected, respectively (experimental group). The remaining 7 mice were administered with 1% BSA solution containing no fatty acid of the same amount as above, instead of LPC, in the same manner (control group). Accordingly, the survival rates of the mice in the experimental- and control groups over the lapse of time were examined. Also, the number of intraperitoneal *E. coli* cells 24 hours after the intraperitoneal injection was measured in accordance with the method described in Reference Example 3. The average values were calculated and exhibited in FIG. 5. As shown in FIGS. 5A and 5B, in the mice of experimental group where LPC was administered, death rate due to septicemia was significantly suppressed (P<0.05) and the number of intraperitoneal *E. coli* cells was also remarkably decreased (P<0.01).

EXAMPLE 6

Therapeutic Effects of 1-Stearoyl LPC in CLP-Induced Sepsis Model

<6-1> In the Case where LPC is Administered 2 and 10 Hours after CLP Surgery, Respectively 14 ICR mice of CLP-induced septicemia model according to Reference Example <1-2> were divided into two groups of 7 mice. 7 mice were administered with 1-stearoyl LPC (Sigma Chemical Co., USA) dissolved in 1% BSA solution containing no fatty acid in an amount of 10 mg/kg by subcutaneous injection 2 and 14 hours after the CLP surgery, respectively (experimental group). The remaining 7 mice were administered with 1% BSA solution containing no fatty acid of the same amount as above in the same manner (control group). The numbers of intraperitoneal *E. coli* cells in the ICR mice of experimental and control groups were measured in accordance with Reference Example 3, 24 hours after the CLP surgery. The average values were calculated and exhibited in FIG. 6A. As shown in FIG. 6A, it could be seen that in the mice of experimental group where LPC was administered, the number of intraperitoneal *E. coli* cells was remarkably decreased (P<0.01).

<6-2> In the Case where LPC is Administered Four Times at Intervals of 12 Hours. 2 Hours after CLP Surgery 40 ICR mice of CLP-induced Sepsis model according to Reference Example <1-2> were divided into four groups of 10 mice. Each 10 ICR mice were intraperitoneally administered with 1-stearoyl LPC (Sigma Chemical Co., USA) dissolved in 1% BSA solution containing no fatty acid in amounts of 5, 10, and 20 mg/kg, respectively, four times at intervals of 12 hours, 2 hours after the CLP surgery (experimental group-1, -2 and -3). The remaining 10 ICR mice were administered only with 1% BSA solution containing no fatty acid (control group). And then, the survival rates of mice in experimental- and control groups were investigated over the lapse of time. The results are shown in FIG. 6B. As shown in FIG. 6B, the survival rate of the mice in experimental groups where LPC was administered was much higher than that of the mice in control group.

<6-3> In the Case where LPC is Administered Four Times at Intervals of 12 Hours. 10 Hours after CLP Surgery In order to investigate whether or not LPC has a therapeutic effect even on cases where septicemia is already developed, 20 ICR mice of CLP-induced Sepsis model according to Reference Example <1-2> were divided into two groups. 10 mice for the experimental group were intraperitoneally administered with 1-stearoyl LPC (Sigma Chemical Co., USA) dissolved in 1% BSA solution containing no fatty acid in an amount of 10 mg/kg, four times at intervals of 12 hours, 10 hours after the CLP surgery. The remaining 10 mice for the control group were administered only with 1% BSA solution containing no fatty acid. Thereafter, the survival rates of ICR mice in experimental- and control groups were investigated over the lapse of time. The results are shown in FIG. 6C. As shown in FIG. 6C, even when septicemia was further developed, LPC showed the excellent therapeutic effect.

EXAMPLE 7

Therapeutic Effects of 1-Oleoyl-LPC and 1-Myristoyl-LPC in CLP-Induced Sepsis Model In order to investigate whether LPCs having other substituents ($R_1$) but 1-stearoyl have an effect on septicemia, LPCs having 1-oleoyl or 1-myristoyl were intraperitoneally administered in an amount of 10 mg/kg according to the same methods as used in Example <6-2>. As a result, as shown in FIG. 7, both 1-oleoyl LPC and 1-myristoyl LPC showed the excellent therapeutic effect against Sepsis.

COMPARATIVE EXAMPLE

In Vitro Antibacterial Activity of LPC 1-stearoyl LPC (Sigma Chemical Co., USA) was added to LB media at concentrations of 12, 60 and 300 mM, respectively, which were poured onto 60-mm petridishes and hardened (experimental group-1, -2 and -3). Four petridishes per group were used. For a control group, only LB media was poured onto four 60-mm petridishes and hardened. The peritoneal cavity of mice according to Example <6-1> was washed with sterilized saline. The resultant solution was diluted with HBSS in a ratio of 1/100, and then 10 μl of the diluted solution was spread on the media for each group. Subsequently, after they had been incubated in a bacteria incubator maintained at 37° C. for 12 hours, colony forming unit (CFU) was visibly measured. The results were summarized in Table I below.

TABLE 1

| | In Vitro Antibacterial Activity of LPC | | | |
|---|---|---|---|---|
| | Control Group | Experimental Group-1 | Experimental Group-2 | Experimental Group-3 |
| LPC conc. | 0 μM | 12 μM | 60 μM | 300 μM |
| CFU | 498 ± 189 | 661 ± 285 | 639 ± 304 | 611 ± 281 |

As shown in Table I above, there appeared no in vitro direct antibacterial effects of LPC against E. coli.

EXAMPLE 8

Effects of SPC in CLP-Induced Sepsis Model

CLP-induced Sepsis model mice were subcutaneously injected with SPC, instead of 1-stearoyl LPC, in dosages of 3 mg/kg and 30 mg/kg four times at intervals of 12 hours, 2 hours after the CLP surgery, respectively. The survival rates of mice were investigated. As a result, as shown in FIG. 8, it could be seen that like LPC, SPC effectively inhibited death rate due to CLP Sepsis at a dosage of 30 mg/kg.

EXAMPLE 9

Therapeutic Effects of LPC Against Acute Respiratory Distress Syndrome

<9-1> LPS-Induced Acute Lung Injury (ALI) Model

Mice were intratracheally administered with LPS to cause direct acute lung injury, thereby inducing acute respiratory distress syndrome.

ICR mice (25-30 g in body weight; MJ Ltd.) were divided into five groups of 7 mice (Sham group, experimental groups-1, -2, -3 and a control group). Mice of each group were anesthetized with pentobarbital, their skins were dissected in a length of 1 cm to expose their bronchia. The mice in Sham group were intratracheally administered with PBS (50 μl) solution and then sutured, while the ICR mice in experimental- and control groups were directly intratracheally administered with LPS (6 μg/50 μl PBS buffer) and then sutured. Thereafter, the ICR mice in the experimental groups-1, -2 and -3 were subcutaneously administered with 1-stearoyl LPC (Sigma Chemical Co., USA) dissolved in 1% BSA solution containing no fatty acid in amounts of 5, 10, and 20 mg/kg, respectively, 2 and 14 hours after LPS had been administered. On the other hand, the ICR mice in a control group were administered with 1% BSA solution containing no fatty acid of the same amount, instead of LPC, in the same manner. At 24 hours after LPS had been administered, the activity of MPO, an indicator of neutrophils, in the pulmonary tissues of the ICR mice of each group was determined as described in Reference Example 2, and the average values are exhibited in FIG. 9A. As shown in FIG. 9A, when LPS was intratracheally administered, the activity of MPO was significantly increased ($p<0.001$). In the ICR mice of experimental groups, the activity of MPO was suppressed in a concentration-dependent manner as compared with the mice of control group. When LPC was administered into ICR mice in an amount of 20 mg/kg (experimental group-3), the most excellent effects were achieved ($p<0.01$).

<9-2> Systemic LPC-Induced Acute Lung Injury Model

Indirect acute lung injury was caused by systemic LPS administration, whereby acute respiratory distress syndrome was induced.

ICR mice in LPS-induced septicemia model according to Reference Example <1-1> b) were divided into five groups of 7 mice (Sham group, an experimental group-1, an experimental group-2, an experimental group-3 and a control group). The mice in Sham group were intraperitoneally administered with PBS buffer (0.5 ml/100 g weight), instead of LPS. The mice in the experimental groups-1, -2 and -3 were subcutaneously administered with 1-stearoyl LPC (Sigma Chemical Co., USA) dissolved in 1% BSA solution containing no fatty acid in amounts of 5, 10, and 20 mg/kg, respectively 2 and 14 hours after LPS had been administered. On the other hands, the mice in a control group were administered with 1% BSA solution containing no fatty acid of the same amount, instead of LPC, in the same manner. At 24 hours after LPS had been administered, the activity of MPO, an indicator of neutrophils, in the pulmonary tissues of the mice of each group, was determined as described in Reference Example 2. The average values are exhibited in FIG. 9B. As shown in FIG. 9B, when LPS was intraperitoneally administered, the activity of MPO was significantly increased ($p<0.01$). In the mice of the experimental groups, the activity of MPO was suppressed in a concentration-dependent manner as compared with the mice of a control group. When LPC was administered into ICR mice in an amount of 20 mg/kg (experimental group-3), the most excellent effects were achieved ($p<0.01$).

<9-3> Acute Lung Injury Model by CLP-Induced Sepsis

The CLP-induced Sepsis model was used to cause indirect acute lung injury, thereby inducing acute respiratory distress syndrome.

20 ICR mice of CLP-induced Sepsis model according to Reference Example <1-2> were divided into two groups. 10 mice for the experimental group were administered with 1-stearoyl LPC (Sigma Chemical Co., USA) dissolved in 1% BSA solution containing no fatty acid in an amount of 10 mg/kg by subcutaneous injection 2 and 14 hours after the CLP surgery, respectively. The remaining 10 mice for the control group were administered only with 1% BSA solution containing no fatty acid. In the meantime, 10 ICR mice (25-30 g in body weight; MJ Ltd.) were anesthetized with pentobarbital, of which right abdominal sites were dissected in a length of 1 cm to expose their cecum, and then sutured again (Sham group). Right after CLP surgery and 4, 8 and 16 hours later, the activity of MPO, an indicator of neutrophils, in the pulmonary tissues of the mice of each group was determined as described in Reference Example 2 and exhibited in FIG. 9C. As shown in FIG. 9C, the activity of MPO was remarkably increased since 4 hours after the CLP surgery and maintained till 16 hours. In the ICR mice of experimental group, the activity of MPO, which had been increased by CLP surgery, was remarkably suppressed as compared with the control group.

EXAMPLE 10

Therapeutic Effects of LPC Against Multiple Organ Dysfunction Syndrome

Septicemia causes multiple organ dysfunction syndrome as its complication and typically, lung, liver, kidney, etc. are injured. The effect of LPC against liver injury as one of the multiple organ dysfuction syndromes was investigated. 20 ICR mice of CLP-induced septicemia model according to Reference Example <1-2> were divided into two groups. 10 mice for the experimental group were administered with 1-stearoyl LPC (Sigma Chemical Co., USA) dissolved in 1% BSA solution containing no fatty acid in an amount of 10 mg/kg by subcutaneous injection 2 and 14 hours after the CLP surgery, respectively. The remaining 10 mice for the control group were administered only with 1% BSA solution containing no fatty acid. In the meantime, 10 ICR mice (25-30 g in body weight; MJ Ltd.) were anesthetized with pentobarbital, of which right abdominal sites were dissected in a length of 1 cm to expose their cecum, and then sutured again (Sham group). At 16 hours after the CLP surgery, blood was collected from mice in each group. The level of alanine aminotransferase (ALT), an indicator of hepatotoxicity, was determined according to the Reitman-Frankel method (Witter & Grubbs, *Clin Chim Acta*, 13:524-7, 1966). As a result, as shown in FIG. 10, in the ICR mice of experimental group, ALT level, which had been increased by CLP surgery, was remarkably suppressed as compared with the control group.

EXAMPLE 11

Effects of LPC on Bactericidal Activity of Neutrophils in Bacteria-Induced Sepsis Model In order to investigate mechanism on how the number of intraperitoneal *E. coli* cells in mice was remarkably decreased due to the administration of LPC in Example 5 above, the inventors conducted the following experiments: Blood was collected from bacteria-induced septicemia model mice prepared in Reference Example <1-1> a), and neutrophils were isolated therefrom. The isolated neutrophils were adhered to the cover slip coated with poly-L-Lysine (0.01%) in a cell incubator maintained at 37° C., at a cell concentration of $10^6$ cells/ml for 1 hour. Thereafter, *E. coli* was added thereto in a concentration of $10^6$ cells/ml and cultured for 1 hour. *E. coli* cells that were not ingested by neutrophils were removed by washing the cover slip with PBS buffer. The cover slip was then treated with 30 μp M 1-stearoyl LPC, and further cultured for another 1 hour. In this stage, the cover slip of the control group was treated with PBS buffer, instead of LPC. Thereafter, after the exchange of a new RPMI-1640 medium, they were further cultured for 1 hour to give killing time. Then, the neutrophils were broken using Triton X-100 (0.05%), and accordingly *E. coli* cells were recovered. The recovered *E. coli* cells were spread onto a plate and cultured in an incubator maintained at 37° C. The number of *E. coli* cells that had grown on the medium was counted and subjected to statistical analysis. As a result, as shown in FIG. 11, in the experimental group that was treated with LPC, the number of alive *E. coli* was significantly decreased. This indicates that LPC increases the bactericidal ability of neutrophils by directly stimulating the neutrophils. Accordingly, it can be seen that LPC blocks the suppressed neutrophil apoptosis, inhibits release of IL-8 in neutrophils/monocytes and also increases the bactericidal activity of neutrophils.

INDUSTRIAL APPLICABILITY

As described in the above, it was identified in the present invention that LPC, SPC and derivatives thereof, agonist ligands specific to G2A receptor, can effectively inhibit the anti-apoptosis of neutrophils and the excessive release of IL-8. In addition, it was revealed that the agonist ligands according to the present invention can effectively eliminate pathogens in microbial infection by increasing the bactericidal activity of neutrophils. Accordingly, the agonist ligands specific to G2A receptor according to the present invention and pharmaceutical- or therapeutical composition comprising the said ligands can be used very effectively in treatment of a disease or disorder associated with neutrophil accumulation and/or excessive release of IL-8, especially inflammatory diseases including sepsis, or a disease associated with microbial infection.

---

What is claimed is:

1. A method for treating sepsis or septic shock comprising administering to a subject in need thereof an effective amount of a compound selected from the group consisting of 18:0 LPC (1-stearoyl lysophosphatidylcholine), 18:1 LPC (1-oleoyl lysophosphatidylcholine), 14:0 LPC (1-myristoyl lysophospatidylcholine), 16:0 LPC (1-palmitoyl lysophosphatidylcholine) and SPC (sphingosylphosphorylcholine).

2. The method of claim 1, wherein the effective amount of the compound is from 0.01 to 100 mg per kg of body weight of the subject in need thereof.

* * * * *